United States Patent [19]

Brown

[11] 4,073,789

[45] Feb. 14, 1978

[54] INDOLOBENZOXAZEPINES

[75] Inventor: Richard E. Brown, Hanover, N.J.

[73] Assignee: Warner-Lambert Company, Morris Plains, N.J.

[21] Appl. No.: 737,969

[22] Filed: Nov. 2, 1976

Related U.S. Application Data

[62] Division of Ser. No. 627,159, Oct. 30, 1975, Pat. No. 4,013,660.

[51] Int. Cl.$^2$ .................................. C07D 491/00
[52] U.S. Cl. .......................... 260/293.58; 260/326.15
[58] Field of Search ...................... 260/293.58, 326.15

[56] References Cited

U.S. PATENT DOCUMENTS 3,813,396  5/1974  Yale et al. .................... 260/268 PC Primary Examiner—Henry R. Jiles
Assistant Examiner—Bernard Dentz
Attorney, Agent, or Firm—Albert H. Graddis; Frank S. Chow; George M. Yahwak

[57] ABSTRACT

This invention relates to substituted indolobenzoxazepines which show neuroleptic activity.

8 Claims, No Drawings

INDOLOBENZOXAZEPINES

This is a division of application Ser. No. 627,159, filed Oct. 30, 1975, now U.S. Pat. No. 4,013,660.

This invention relates to substituted indolobenzoxazepines of the following general formula:

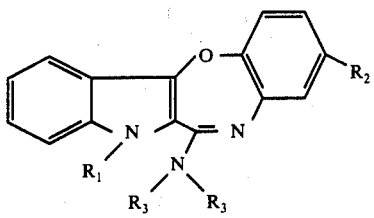
I

In this formula, $R_1$ may be hydrogen, lower alkyl of 1 to 6 carbon atoms or an aralkyl group of 1 to 6 carbon atoms in the chain; $R_2$ may be hydrogen, lower alkyl of 1 to 6 carbon atoms, a trifluoromethyl group or a halogen atom such as chlorine or fluorine and $R_3$ may be hydrogen, lower alkyl of 1 to 6 carbon atoms, a di-lower alkylamino group, or taken together with the nitrogen may form a heterocyclic ring of the formula

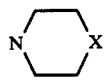

wherein X may be oxygen, sulfur, —$CH_2CH_2$—, a bond connecting the adjacent carbon atoms or CH—$R_4$ or N—$R_4$, wherein $R_4$ may be hydrogen or lower alkyl of 1 to 6 carbon atoms, or $R_3$ may be an ω-aminoalkyl group of the formula

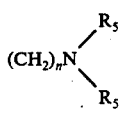

wherein n may be 2 to 4, and $R_5$ may be hydrogen, lower alkyl of 1 to 6 carbon atoms or taken together may form a heterocyclic ring of the formula

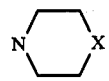

wherein X is as described above.

The compounds of this invention may be prepared using a lactam of the general formula II as starting material. These starting materials are described in our co-pending patent application, U.S. Pat. No. 620,734 now U.S. Pat. No. 4,013,641. These starting lactams are first treated with a reagent to reactivate the carbonyl group, and the intermediates thus formed are further treated with the appropriate amine to form the final products of structure I. Among the reagents

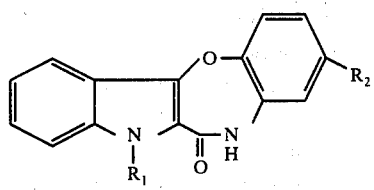
II which may be used to activate the carbonyl group are phosphorus pentachloride and triethyloxonium fluoroborate. The activated intermediates may be isolated but in most cases are conveniently treated, without isolation, with an excess of the appropriate amine. The entire operation is generally carried out in one step using an excess of the amine as solvent. Alternatively, a nonpolar solvent such as benzene or carbon tetrachloride may be used.

In order to further illustrate the subject matter of this invention, I have included the following examples:

EXAMPLE 1

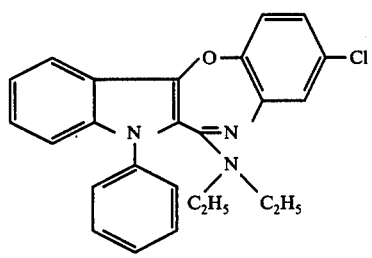

7-benzyl-3-chloro-6(diethylamino)-7H-indolo[3,2-b]-1,5]benzoxazepine

A mixture of 7.48g of 3-chloro-7-benzyl-7H-indolo[3,2-b][1,5]benzoxazepine-6(5H)-one and 5.25g of phosphorus pentachloride in 200ml of benzene was stirred at reflux for 4½ hours. A yellow solid precipitated. To this suspension was added at reflux with stirring, 14.6g of diethylamine. The reaction was stirred at reflux for another 2 hours, cooled, diluted with an equal volume of ether, washed twice with $H_2O$, dried and concentrated to an orange oil. The oil crystallized on rubbing with ethanol. Recrystallization for ethanol gave analytical material, mp. 132°-4°.

Anal. Calcd. for $C_{26}H_{24}N_3OCl$: C, 72.63; H, 5.63; N, 9.77; Cl, 8.25. Found: C, 72.50; H, 5.66; N, 9.78; Cl, 8.49.

EXAMPLE 2

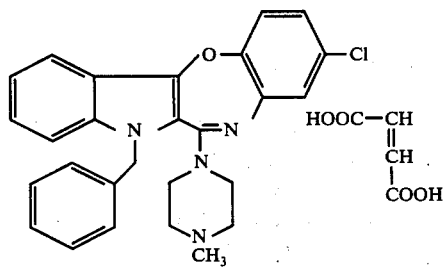

7-benzyl-3-chloro-6-(4-methyl-1-piperazinyl)-7H-indolo[3,2-b][1,5]benzoxazepine fumarate.

In the same way as described in example 1, 3-chloro-7-benzyl-7H-indolo[3,2-b][1,5]benzoxazepine-6(5H)-one, phosphorus pentalchloride and N-methyl piperazine were reacted. The product was purified by chromatography on neutral alumina and elution with 3% ethanol in ether. The yellow oil thus obtained was reacted with fumaric acid in hot ethanol and the salt recrystallized from ethanol for analysis, mp. 217°–8°.

Anal. Calcd. for $C_{27}H_{25}N_4OCl \cdot C_4H_4O_4$: C, 64.98; H, 5.10; N, 9.78; Cl, 6.19. Found: C, 64.88; H, 5.14; N, 9.90; Cl, 6.20.

EXAMPLE 3

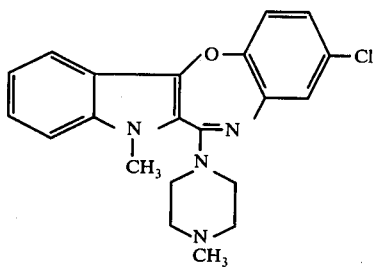

3-chloro-7-methyl-6(4-methyl-1-piperazinyl)-7H-indolo[3,2-b][1,5]benzoxazepine.

In the same way as described in example 1, 3-chloro-7-methyl-7H-indolo[3,2-b][1,5]benzoxazepine-6(5H)-one, phosphorous pentachloride and N-methyl piperazine were reacted. The solid product was recrystallized from ethanol for analysis, mp. 187°–8°.

Anal. Calcd. for $C_{21}H_{21}N_4OCl$: C, 66.22; H, 5.56; N, 14.71; Cl, 9.31. Found: C, 65.97; H, 5.57; N, 14.94; Cl, 9.13.

EXAMPLE 4

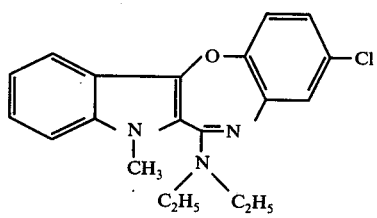

3-chloro-6(diethylamino)-7-methyl-7H-indolo[3,2-b][1,5]benzoxazepine

In the same way as described in example 1, 3-chloro-7-methyl-7H-indolo [3,2-b][1,5]benzoxazepine-6(5H)-one, phosphorus pentachloride and diethylamine were reacted and the solid product recrystallized from methanol for analysis, mp. 127°–8°.

Anal. Calcd. for $C_{20}H_{20}N_3OCl$: C, 67.89; H, 5.70; N, 11.88; Cl, 10.02. Found: C, 68.09; H, 5.77; N, 11.71; Cl, 10.21.

EXAMPLE 5

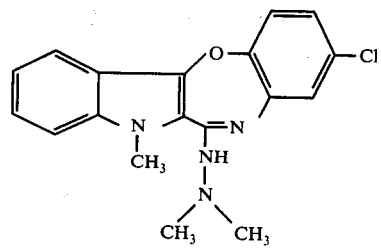

3-chloro-6-(2,2-dimethylhydrazino)-7-methyl-7H-indolo[3,2-b][1,5]benzoxazepine.

In the same way as described in example 1, 3-chloro-7-methyl-7H-indolo[3,2-b[]1,5]benzoxazepine and dimethylhydrazine were reacted. The crude product was recrystallized from acetonitrile for analysis, mp. 196°–7°.

Anal. Calcd. for $C_{18}H_{17}N_4OCl$: C, 63.44; H, 5.03; N, 16.44; Cl, 10.40. Found: C, 63.43; H, 5.06; N, 16.36; Cl, 10.62.

EXAMPLE 6

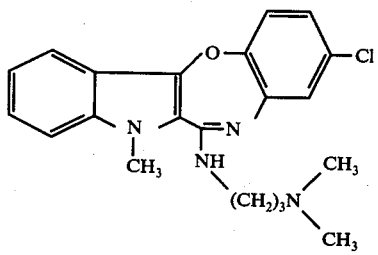

3-chloro-6-{[3-(dimethylamino)propyl]amino}-[7-methyl-7H-indolo[3,2-b][1,5]benzoxazepine In the same way as described in example 1, 3-chloro-7-methyl-7H-indolo[3,2-b][1,5]benzoxazepine-6(5H)-one, phosphorous pentachloride and 3-dimethylaminopropylamine were reacted and the crude product recrystallized from acetonitrile for analysis, mp. 156°–7°.

Anal. Calcd. for $C_{21}H_{23}N_4OCl$: C, 65.88; H, 6.06; N, 14.63; Cl, 9.26. Found: C, 65.87; H, 6.17; N, 14.73; Cl, 9.52.

EXAMPLE 7

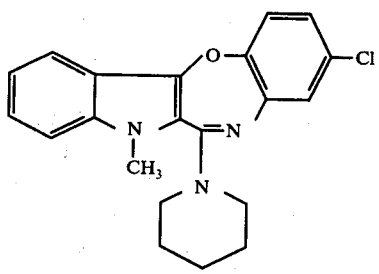

3-chloro-7-methyl-6-piperidino-7H-indolo[3,2-b][1,5]benzoxazepine

A solution of 5.0g of 3-chloro-7-methyl-7H-indolo[3,2-b][1,5]benzoxazepine-6(5H)-one in 60ml of methylene chloride was cooled to 15° and treated with 30ml of a 1N solution of triethyloxonium fluoroborate in methylene chloride. The mixture was stirred for 48 hrs. at ambient temperature. The precipitated solid was filtered, washed with methylene chloride and added to 10ml of piperidine, and the clear solution was heated for 8 hrs. on the steam bath. The mixture was diluted with water, and the precipitated solid was filtered and recrystallized from ethylacetate, mp. 244°–5°.

Anal. Calcd. for $C_{21}H_{20}N_3OCl$: C, 68.94; M,5.51; N 11.49; Cl, 9.69. Found: C, 69.02; H, 5.51; N, 11.37; Cl, 9.85.

The compounds of this invention possess CNS depressant properties and as such are valuable as neuroleptic agents; for example, the compound according to structure III is

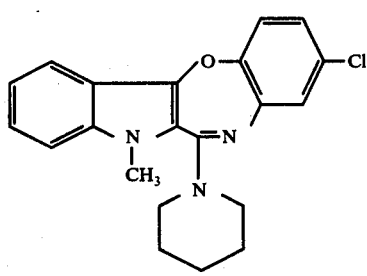

III very active at an intraperitonial dose of 25 mg/kg in calming mice made agressive by isolation (the test procedure of Yen, Stanger and Millman, Arch. Int. Pharmacodyn., 123: 179 (1959)). In addition, the compound of structure IV, when tested according to the procedure of Anden and Stock (J. Pharm. and Pharmacol., 25: 348 (1973)) in subcortical regions of the brain, elevated homovanilic acid levels in the same way as known neuroleptics.

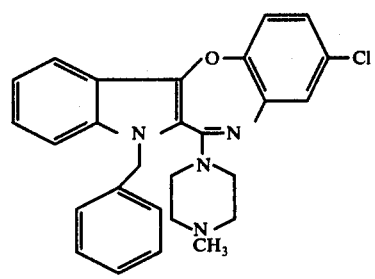

IV

I claim:

1. A compound of the formula:

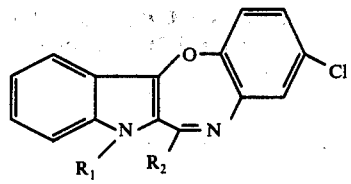

I wherein $R_1$ is

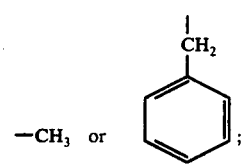

$R_2$ is

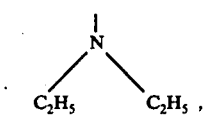

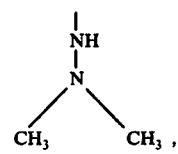

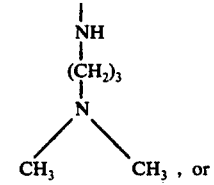

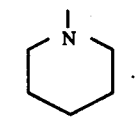

2. A compound according to claim 1 wherein $R_1$ is

3. The compound of claim 2 which is 3-chloro-6-(diethylamino)-7-(phenylmethyl)-7H-indolo-[3,2-b][1,5]benzoxazepine.

4. A compound according to claim 1 wherein $R_1$ is —CH$_3$.

5. The compound of claim 4 which is 3-chloro-N,N-diethyl-7-methyl-7H-indolo[3,2-b][1,5]-benzoxazepine-6-amine.

6. The compound of claim 4 which is 3-chloro-6-(2,2-dimethylhydrazino)-7-methyl-7H-indolo-[3,2-b][1,5]benzoxazepine.

7. The compound of claim 4 which is N'-(3-chloro-7-methyl-7H-indolo [3,2-b][1,5]benzoxazepin-6-yl)-N,N-dimethyl-1,3-propanediamine.

8. The compound of claim 4 which is 3-chloro-7-methyl-6-(1-piperidinyl)-7H-indolo-[3,2-b][1,5]benzoxazepine.

* * * * *